US010392321B2

(12) United States Patent
Garg et al.

(10) Patent No.: US 10,392,321 B2
(45) Date of Patent: Aug. 27, 2019

(54) PROCESSES FOR TRANSALKYLATING AROMATIC HYDROCARBONS

(71) Applicant: UOP LLC, Des Plaines, IL (US)

(72) Inventors: Nishesh Garg, Chandigarh (IN); Stephen W. Sohn, Arlington Heights, IL (US); Amit Sharma, Gurgaon (IN); Priyesh J. Jani, Gurgaon (IN); Sarbotrika Sengupta, Kolkata (IN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/975,655

(22) Filed: May 9, 2018

(65) Prior Publication Data

US 2019/0194093 A1 Jun. 27, 2019

Related U.S. Application Data

(60) Provisional application No. 62/610,767, filed on Dec. 27, 2017.

(51) Int. Cl.
*C07C 6/06* (2006.01)
*C07C 2/04* (2006.01)

(52) U.S. Cl.
CPC . *C07C 6/06* (2013.01); *C07C 2/04* (2013.01)

(58) Field of Classification Search
None
See application file for complete search history.

(56) References Cited

U.S. PATENT DOCUMENTS

| | | | |
|---|---|---|---|
| 973,201 A | 10/1910 | Jordan | |
| 6,867,340 B2 | 3/2005 | Oh et al. | |
| 7,425,659 B2 * | 9/2008 | Clark | B01J 8/001 585/467 |
| 7,576,247 B2 * | 8/2009 | Sohn | C07C 2/66 585/323 |
| 7,692,055 B2 | 4/2010 | Sohn et al. | |
| 7,803,977 B2 | 9/2010 | Riley et al. | |
| 8,148,592 B2 | 4/2012 | Goncalvez et al. | |
| 9,732,014 B2 | 8/2017 | Sohn et al. | |
| 9,751,817 B2 | 9/2017 | Jani et al. | |
| 2008/0194894 A1 | 8/2008 | Sohn et al. | |
| 2011/0144403 A1 | 6/2011 | Jan et al. | |
| 2016/0090338 A1 * | 3/2016 | Geltz | C07C 6/126 585/467 |

FOREIGN PATENT DOCUMENTS

CN 101811063 B 10/2012

OTHER PUBLICATIONS

PCT Search Report dated Apr. 11, 2019 for PCT International Application No. PCT/US/2018/067481.

\* cited by examiner

*Primary Examiner* — Philip Y Louie
*Assistant Examiner* — Alyssa L Cepluch

(57) ABSTRACT

Processes for transalkylation of aromatic hydrocarbons is disclosed. The process includes introducing a feed stream comprising aromatic hydrocarbon compounds to a transalkylation zone. A water source is introduced to the transalkylation zone, the water source being in an amount to provide about 80 to about 120 wppm of water based upon the mass of the feed stream. The feed stream is contacted with a transalkylation catalyst in the transalkylation zone under transalkylation conditions comprising a transalkylation temperature of about 130° C. to about 230° C. in the presence of the water to provide a transalkylation reaction effluent.

20 Claims, 1 Drawing Sheet

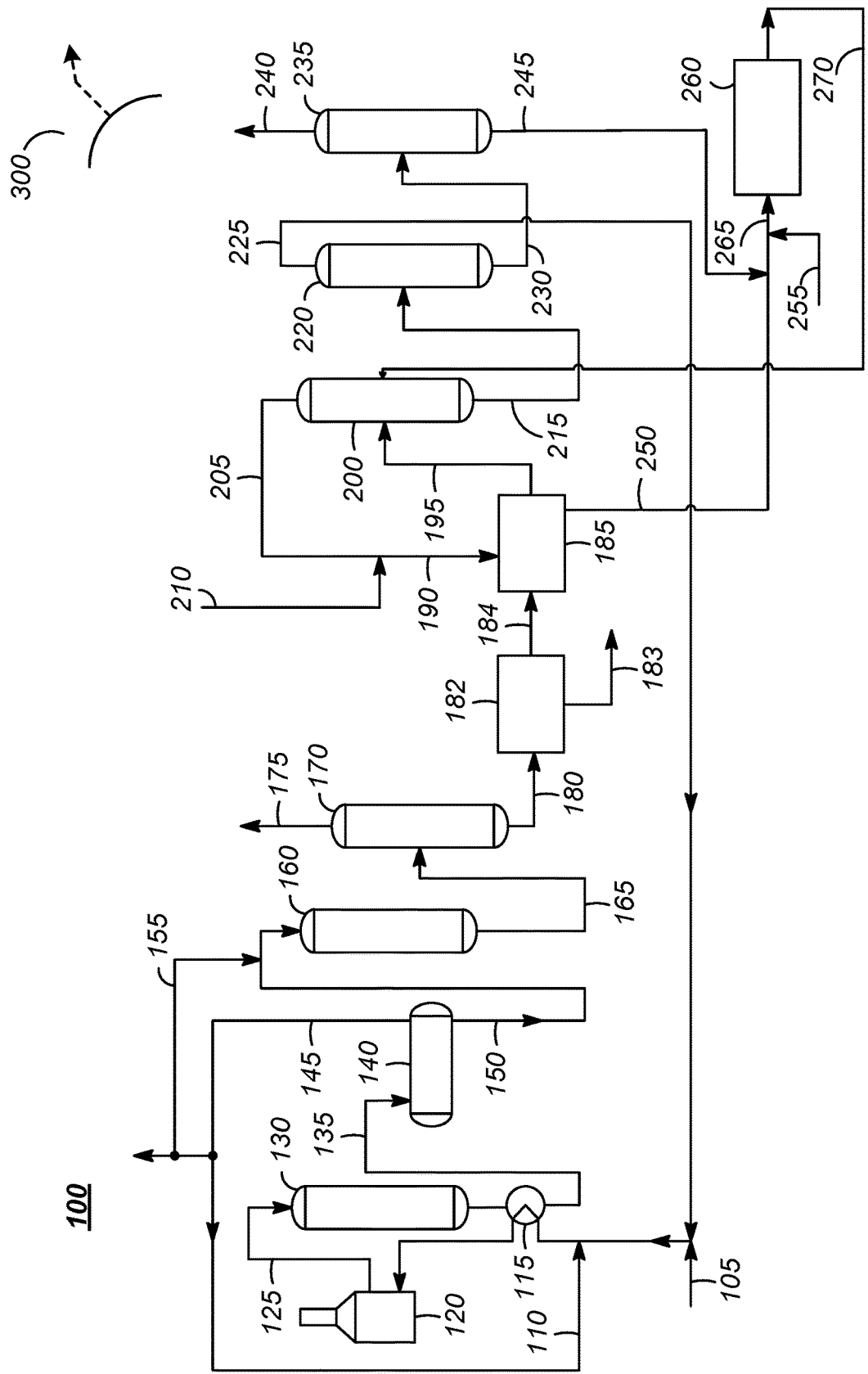

PROCESSES FOR TRANSALKYLATING AROMATIC HYDROCARBONS

CROSS-REFERENCE TO RELATED APPLICATION

This application claims priority from Provisional Application No. 62/610,767 filed Dec. 27, 2017, the contents of which cited application are hereby incorporated by reference in its entirety.

FIELD

The subject matter relates to improved processes for transalkylating aromatic hydrocarbon compounds. More particularly, the present disclosure relates to improvement of transalkylation catalyst activity by addition of water in a processes for transalkylating aromatic hydrocarbon compounds.

BACKGROUND

Typically, in a transalkylation process, a heavy alkylbenzene (HAB) byproduct is trans-alkylated with benzene to form additional linear alkyl benzene (LAB) product resulting in an increase in desired linear alkylbenzene product with no increase in the paraffin/olefin feed input. Also, the resulting LAB is comparable in quality to LAB produced in the alkylation process.

However, it has been noted that the HAB conversion is quite low when using with a conventional transalkylation catalyst. Replacing the conventional catalyst with a denser and less acidic catalyst results in catalyst poorer performance due to the reduced acidic nature of the catalyst.

Therefore, there is a need for an improved transalkylation processes and apparatuses for achieving the desired HAB conversion. There is a need for improving the activity of the transalkylation catalyst to achieve a desired conversion level without deterioration of catalyst performance being deteriorated. Other desirable features and characteristics of the present subject matter will become apparent from the subsequent detailed description of the subject matter and the claims, taken in conjunction with the accompanying drawing and this background of the subject matter.

SUMMARY

Various embodiments of an improved processes for transalkylating aromatic hydrocarbon compounds are provided. The process includes addition of water to the transalkylation process to improve the transalkylation catalyst activity in a processes for transalkylating aromatic hydrocarbon compounds.

In accordance with an exemplary embodiment, a process is provided for transalkylating aromatic hydrocarbon compounds, the process comprising introducing a feed stream comprising aromatic hydrocarbon compounds to a transalkylation zone. A water source is introduced to the transalkylation zone, the water source being in an amount to provide about 80 to about 120 wppm of water based upon the mass of the feed stream. The feed stream is contacted with a transalkylation catalyst in the transalkylation zone under transalkylation conditions comprising a transalkylation temperature of from about 130° C. to about 230° C. in the presence of the water to provide a transalkylation reaction effluent.

In accordance with another exemplary embodiment, a process is provided for transalkylating aromatic hydrocarbon compounds, the process comprising contacting benzene and an olefin in an alkylation zone under alkylation conditions in the presence of an alkylation catalyst to produce an alkylation product comprising benzene, linear monoalkylbenzenes and heavy alkylbenzenes. The alkylation product is separated to provide a monoalkylbenzene rich stream and a heavy alkylbenzene rich stream. A feed stream comprising a benzene rich stream from the alkylation zone and the heavy alkylbenzene rich stream is introduced to a transalkylation zone. A water source is introduced to the transalkylation zone, the water source being in an amount to provide about 80 to about 120 wppm of water based upon the mass of the feed stream. The feed stream is contacted with a catalyst in the transalkylation zone under transalkylation conditions comprising a transalkylation temperature of from about 130° C. to about 230° C. including the presence of water to provide a transalkylation reaction effluent.

These and other features, aspects, and advantages of the present disclosure are further explained by the following detailed description, drawing and appended claims.

BRIEF DESCRIPTION OF THE DRAWING

The various embodiments will hereinafter be described in conjunction with the FIGURE, wherein like numerals denote like elements.

The FIGURE is a schematic representation of an alkylbenzene complex using the processes of the present disclosure.

Skilled artisans will appreciate that elements in the FIGURE are illustrated for simplicity and clarity and have not necessarily been drawn to scale. For example, the dimensions of some of the elements in the FIGURE may be exaggerated relative to other elements to help to improve understanding of various embodiments of the present disclosure. Also, common but well-understood elements that are useful or necessary in a commercially feasible embodiment may not be depicted in order to facilitate a less obstructed view of these various embodiments of the present disclosure.

DETAILED DESCRIPTION

Various embodiments herein relate to processes for the treatment of spent alkaline stream. As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$ ... Cn where "n" represents the number of carbon atoms in the one or more hydrocarbon molecules. Furthermore, a superscript "+" or "−" may be used with an abbreviated one or more hydrocarbons notation, e.g., $C_{3-}$ or $C_{3-}$, which is inclusive of the abbreviated one or more hydrocarbons. As an example, the abbreviation "$C_{3+}$" means one or more hydrocarbon molecules of three carbon atoms and/or more. In addition, the term "stream" may be applicable to other fluids, such as aqueous and non-aqueous solutions of alkaline or basic compounds, such as sodium hydroxide.

As used herein, the term "zone" can refer to an area including one or more equipment items and/or one or more units. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "parts per million" may be abbreviated herein as "ppm" and unless otherwise specified it refers to "weight ppm", abbreviated herein as "wppm".

As used herein, the term "weight percent" may be abbreviated "wt. %" and unless otherwise specified the notation "%" refers to "wt. %".

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "rich" can mean an amount of at least generally about 80%, or about 90%, and or about 99%, by mole, of a compound or class of compounds in a stream.

As used herein, the term "linearity" is the mass percent of normal alkylbenzenes to total alkylbenzenes.

As depicted, process flow lines in the FIGURE can be referred to, interchangeably, as, e.g., lines, pipes, branches, distributors, streams, effluents, feeds, products, portions, catalysts, withdrawals, recycles, suctions, discharges, and caustics.

The aromatic compound used in the alkylation process can be any suitable aromatic compound, including, but not limited to, benzene, toluene, ethylbenzene, xylenes, or combinations thereof. Benzene is the most commonly used aromatic compound. Consequently, benzene will be used for ease of discussion.

The transalkylation process as discussed herein may be integrated into a system for the production of linear alkylbenzenes from benzene and olefins. The process comprises continuously supplying benzene and a mixture of olefins, wherein the olefins are a mixture of linear olefins having 8 to 16 carbons, to an alkylation zone. The alkylation zone is operated at alkylation conditions in the presence of an alkylation catalyst, and generates an effluent stream having benzene, linear monoalkylbenzenes and heavy alkylbenzenes.

Heavy alkylbenzene (HAB) are compounds which may include dialkylbenzenes comprising between about $C_{26}$-$C_{32}$ hydrocarbons and diphenylalkanes comprising between about $C_{22}$ to $C_{25}$ hydrocarbons. The range of carbon numbers specified herein are based on processing a feed stream including benzene and $C_{10-13}$ olefins.

The desired alkylated compounds are monoalkylated aromatic compounds. Two common reactions for producing monoalkylated aromatic compounds are alkylation of aromatic compounds such as benzene, and transalkylation of polyalkylated aromatic compounds. Monoalkylated aromatic compounds include linear alkylbenzenes (LAB), which are used to form linear alkylbenzene sulfonates (LABS), a common compound used in detergents, and which are manufactured from linear alkylbenzenes. One aspect of benzene alkylation has been the use of high benzene to olefin ratios for the production of alkylbenzene production.

Integrated processes for producing LABs using solid alkylation catalysts have been developed. An example of an integrated process is shown in the FIGURE which includes a dehydrogenation process, followed by a selective catalytic hydrogenation process, an alkylation process and a transalkylation process. As shown in the FIGURE, the integrated process and apparatus 100 includes a charge heater 120, a dehydrogenation zone 130, a separator 140, a selective hydrogenation reactor 160, a stripper 170, an aromatics removal zone 182, an alkylation zone 185, a benzene distillation column 200, a paraffin distillation column 220 and a transalkylation zone 260.

As shown in the FIGURE, a paraffin feed in line 105 may be mixed with a hydrogen stream in line 110 and passed through a heat exchanger 115 and the charge heater 120 to provide a heated stream in line 125. The heated stream in line 125 may be passed to the dehydrogenation zone 130. A hydrogenation effluent is withdrawn in line 135 from the dehydrogenation zone 130. The dehydrogenation effluent in line 135 exchanges heat with the paraffin feed in line 105 and hydrogen stream in line 110 in the heat exchanger 115. Subsequently, the dehydrogenation effluent may be passed to a separator 140 and separated into a hydrogen gas stream in line 145 and a liquid stream 150. The liquid stream 150 may be mixed with hydrogen in line 155 and passed to the selective hydrogenation zone 160 where any diolefins are hydrogenated to mono-olefins.

A selective hydrogenation zone effluent may be withdrawn in line 165 from the selective hydrogenation reactor 160 and passed to the stripper 170 where light ends are removed in line 175 from an overhead and a bottoms stream in line 180 is withdrawn. The bottoms stream in line 180 from the stripper 170 may be sent to the aromatics removal zone 182 where aromatics are removed in line 183. A treated stream rich in olefins is withdrawn in line 184 from the aromatics removal zone 182. The treated stream 184 is sent to the alkylation zone 185 where it is mixed with a benzene stream in line 190. In the alkylation zone 185, benzene and an olefin are contacted under alkylation conditions in the presence of an alkylation catalyst to produce an alkylation product in line 195 comprising benzene, linear monoalkylbenzenes and heavy alkylbenzenes. Subsequently, the alkylation product may be separated to provide a monoalkylbenzene rich stream and a heavy alkylbenzene rich stream. In accordance with an exemplary embodiment as shown in the FIGURE, the alkylation product in line 195 may be passed to the benzene distillation column 200 to provide a benzene column overhead stream in line 205 and a benzene column bottoms stream in line 215.

The benzene distillation is generally conducted with a bottoms temperature of less than about 300° C., preferably less than about 275° C., usually between about 230° C. and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column used for benzene distillation may contain any convenient packing or distillation trays; often trays such as sieve and bubble trays, are used. Often the assembly provides at least about 5 theoretical plates, for example, 6 to 70, or 20 to 50. The reflux ratio is often in the range of about 2:1 to 1:10, or about 1.5:1 to 1:5. The bottoms stream from the benzene distillation generally contains less than about 1000 ppmw, or less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The benzene column overhead stream in line 205 may be mixed with fresh benzene stream in line 210 to form the benzene stream in line 190. The benzene column bottoms stream in line 215 from the benzene distillation column 200 may be passed to the paraffin distillation column 220 to provide a paraffin column overhead stream in line 225 and a paraffin column bottoms stream in line 230. The paraffin distillation is generally conducted with a bottoms temperature of less than about 300° C., or less than about 275° C., usually between about 250° C. and 275° C., and at a pressure at which overhead is provided of between about 5 and 110 kPa absolute, or between about 10 and 50 kPa absolute. The column may contain any convenient packing or distillation trays, but most often sieve trays are used. Often the paraffins distillation assembly provides at least about 5 theoretical plates, or about 7 to about 20. The reflux ratio is often in the range of about 3:1 to 1:10, or about 1:1 to 1:3. The bottoms stream from the paraffins distillation generally contains less than about 5000, or less than about 500, parts by million by weight (ppmw) paraffins and less than about 10, often less than about 1, ppmw benzene. The paraffins distillation may occur in a single column, or two or more distinct columns may be used.

The paraffin overhead stream in line 225 may be mixed with paraffin feed in line 105 and passed to the dehydrogenation zone 130. The paraffin column bottoms stream in line 230 may be passed to an alkylbenzene distillation column 235 where it is separated into an a monoalkylbenzene rich stream in line 240 containing the monoalkylbenzene from an overhead and a heavy alkylbenzene rich stream in line 245 containing heavy alkylbenzene (e.g., dialkylbenzene) from a bottom. The alkylbenzene distillation is generally conducted with a bottoms temperature of less than about 300° C., or less than about 275° C., usually between about 250° C. and 275° C., and at a pressure of between about 0.5 and 30 kPa absolute, or between about 1 and 5 kPa absolute. The column may contain any convenient packing or distillation trays, but most often structured packing is used. Often the heavy alkylbenzene distillation assembly provides at least about 5 theoretical plates, for example 10 to 30, or 10 to 20. The reflux ratio is often in the range of about 2:1 to 1:5, or about 0.2:1 to 1:1. The overhead from the heavy alkylbenzene distillation generally contains less than about 1000 ppmw, or less than about 100 ppmw, and sometimes less than about 50 ppmw, total heavy alkylbenzene. The monoalkylbenzene rich stream can be further processed, for example, in a finishing column (not shown), if desired. The heavy alkylbenzene rich stream can be further processed, for example, in a transalkylation unit with benzene, to further enhance the yield of monoalkylbenzene, if desired. As shown in the FIGURE, the heavy alkylbenzene rich stream in line 245 may be passed to the transalkylation zone 265, as described later.

Referring back to the alkylation zone 185, as shown in the FIGURE, a benzene rich stream in line 250 may also be withdrawn from the alkylation zone 185. In accordance with an exemplary embodiment, the alkylation zone 185 may include at least a first alkylation reactor and a second alkylation reactor (not shown). The alkylation reactors are typically operated simultaneously, the first alkylation reactor in an alkylation process cycle and the second alkylation reactor in a regeneration cycle. The cycle time is generally about 24 hrs for both the alkylation process cycle and the regeneration cycle. The second alkylation reactor is regenerated by passing a benzene stream through the second alkylation zone at a regeneration temperature above an alkylation temperature to provide a regeneration benzene stream, wherein the benzene rich stream comprises at least a portion of the regeneration benzene stream. In operation, the second alkylation reactor is heated from the alkylation temperature (typically 80° C. and about 200° C., most usually at a temperature not exceeding about 175° C., or about 100° C. to 160° C., or about 120° C. to about 150° C., or about 130° C. to about 140° C.) to the regeneration temperature (typically about 160° C. to about 250° C., or about 180° C. to about 250° C.), which takes about 8 hr. The second alkylation reactor is maintained at the regeneration temperature for a period of time, typically about 8 hr. Then the reactor is cooled down to the alkylation temperature, which generally takes about 8 hr.

Regeneration typically takes place at a pressure in the range of about 1.300 MPa(g) to about 7.000 MPa(g), or about 2.758 MPa (400 psig) to about 4.137 MPa (600 psig), or about 3.44 MPa (500 psig). The system is operated so that the benzene is in the liquid phase at the operating temperatures.

At least a portion of the regeneration benzene stream from the second alkylation reactor is routed to the transalkylation reactor. As shown in the FIGURE, the benzene rich stream in line 250 comprises at least a portion of the regeneration benzene stream. In an embodiment, the entire regeneration benzene stream is sent to the transalkylation zone 265. In some embodiments, a portion of the benzene regeneration stream may be passed to the first alkylation reactor. A portion can also be sent to the benzene distillation column 200, if desired.

The use of regeneration benzene for transalkylation can partially or completely replace the use of fresh benzene in the transalkylation reactor and reduce the amount of benzene from the aromatics removal unit.

Further details, specifics and variations regarding the operation of the alkylation zone comprising the at least first alkylation reactor in process cycle and at least second alkylation reactor in regeneration cycle are described in U.S. Pat. No. 973,201 and U.S. Pat. No. 9,751,817, incorporated herein by reference in their entireties.

Referring back to the transalkylation zone 260, a feed stream comprising aromatic hydrocarbon compounds is introduced to the transalkylation zone 260. In an embodiment, the feed stream comprises benzene to heavy alkylbenzene in a molar ratio of about 15:1 to about 65:1. The heavy alkylbenzene rich stream in line 245 and a benzene rich stream in line 250 may be passed to the transalkylation zone 260. Further, a water source in line 255 may be introduced to the transalkylation zone. The water source is in an amount to provide about 80 to about 120 wppm, or about 100 to about 120 wppm of water, based upon the mass of the feed stream. As shown in the FIGURE, the heavy alkylbenzene rich stream in line 245, the benzene rich stream in line 250 and the water source in line 255 may be mixed to provide a mixed stream in line 265 which may be subsequently passed to the transalkylation reactor 260.

In the transalkylation zone 260, the feed stream is contacted with a transalkylation catalyst under transalkylation conditions comprising a transalkylation temperature of from about 130° C. to about 230° C., or from about 170° C. to about 200° C., in the presence of the water to provide a transalkylation reaction effluent. The transalkylation catalyst may be selected from amorphous silica-alumina, fluorided amorphous silica-alumina, acidic clays, pillared clays, mesoporous crystalline materials, solid phosphoric acid, AlCl3, alumino-phosphates, heteropolyacids, sulfate metal oxides, mixed metal oxides, UZM-5, UZM-8, large pore molecular sieves, and mixtures thereof. In an embodiment, the transalkylation catalyst comprises acidic clays selected from montmorillonite, beidellite, hectonite, saponite, and mixtures thereof. In one embodiment, the transalkylation catalyst comprises a montmorillonite clay. Applicants have found that deactivation rate for the transalkylation catalyst is the lowest and a desired conversion level (more than 50%) is achieved when the transalkylation temperature is between greater than about 130° C. and less than about 230° C. and water is about 80 wppm or about 120 wppm. Further, the heavy alkylbenzene conversion does not cross 50% when either the temperature is decreased to about 130° C. or below or when the temperature is increased above about 230° C. or the water level is less than about 80 wppm or more than about 120 wppm.

A transalkylation reaction effluent in line 270 may be withdrawn from the transalkylation zone 260. The transalkylation reaction effluent may be passed to the benzene distillation column 200 for further processing as previously described.

Applicants have surprisingly found out that addition of water in the amount as disclosed above provides a number of advantages in terms of improvement in overall activity and stability of the catalyst. Further, applicants have found that catalyst pre-drying step with benzene is also not required in the instant process.

The linear alkylbenzene (LAB) obtained according to the process of the present disclosure displays surprisingly better characteristics in term of purity and overall linearity. The contents of cyclic compounds, such as dialkyl-tetralins and dialkyl-indanes are reduced to values lower than 2%, or lower than 1%, and the linear alkylbenzenes reach purity values higher than 95%. Such purity values reduce the need for burdensome process of subsequent purification by treatment with sulphuric acid in order to obtain end alkylbenzene sulfonates with light color and good stability over time.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. The FIGURE shows the above categorically as 300.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein. The FIGURE shows the above categorically as 300.

EXAMPLE

The performance of a heavy alkylbenzene (HAB) transalkylation catalyst was studied over the temperature range 120° C. to 240° C. Controlled moisture injection (online) was done to a feed stream comprising pre-dried benzene and heavy alkylbenzene to maintain target moisture level in feed, ranging from <5 to 500 wppm. The overall HAB conversion was measured at varying temperatures and water levels and deactivation rate of catalyst was calculated. Below table summarizes the operating conditions (temperature and water) and important results (HAB conversion and deactivation rate).

TABLE 1

| Temperature, (Deg ° C.) | HAB Conversion, wt % | Water, wppm | Deactivation Rate, wt %/hr |
|---|---|---|---|
| 130 | 45 | | |
| 150 | 60 | <20 | >0.5 |
| 150 | 60 | <40 | 0.25 |
| 170 | 60 | <5 | 0.4 |
| 170 | 68 | 80 | 0.18 |
| 170 | 70 | 100 | 0.12 |
| 170 | 71 | 120 | 0.12 |
| 170 | 39 | 500 | 0.25 |
| 180 | 80 | <5 | 0.4 |
| 180 | 80 | 100 | 0.1 |
| 180 | 80 | 120 | 0.1 |
| 180 | 40 | 500 | 0.3 |
| 200 | 20 | <5 | 0.4 |
| 200 | 85 | 100 | 0.05 |
| 200 | 85 | 120 | 0.05 |
| 200 | 44 | 500 | 0.25 |
| 230 | <50 | | |

As shown in the above table 1, deactivation rate is the lowest and a desired conversion level (more than 50%) is achieved when the transalkylation temperature is between greater than about 130° C. and less than about 230° C. and water is about 80 wppm or about 120 wppm. Other combination of temperature and water where either the temperature is below about 130° C. and above about 230° C. or the water level is below about 80 wppm and above about 120 wppm results in a lower conversion and/or high deactivation rate. Further, the heavy alkylbenzene conversion does not cross 50% or the deactivation rate is more than about 0.2 wt. %/hr. when either the temperature is decreased to about 130° C. or when the temperature is increased to about 230° C. or the water level is less than about 80 wppm or more than about 120 wppm. Further, during majority of the catalyst life the linearity of the product obtained was more than about 92%.

Specific Embodiments

While the following is described in conjunction with specific embodiments, it will be understood that this description is intended to illustrate and not limit the scope of the preceding description and the appended claims.

A first embodiment of the invention is a process for transalkylating aromatic hydrocarbon compounds, the process comprising a) introducing a feed stream comprising aromatic hydrocarbon compounds to a transalkylation zone; b) introducing a water source to the transalkylation zone, the water source being in an amount to provide about 80 to about 120 wppm of water based upon the mass of the feed stream; and c) contacting the feed stream with a transalkylation catalyst in the transalkylation zone under transalkylation conditions comprising a transalkylation temperature of about 130° C. to about 230° C. in the presence of the water to provide a transalkylation reaction effluent. An embodiment of the invention is one, any or all of prior embodiments in this paragraph up through the first embodiment in this paragraph, wherein the step of introducing the feed stream comprises introducing a heavy alkylbenzene rich stream and a benzene rich stream to the transalkylation zone. An embodiment of the invention is one, any or all of prior embodiments in this paragraph up through the first embodiment in this paragraph, wherein the feed stream comprises benzene to heavy alkylbenzene in a molar ratio of about 15:1 to about 65:1. An embodiment of the invention is one, any or all of prior embodiments in this paragraph up through the first embodiment in this paragraph, wherein the transalkylation catalyst is selected from amorphous silica-alumina, fluorided amorphous silica-alumina, acidic clays, pillared clays, mesoporous crystalline materials, solid phosphoric acid, AlCl3, alumino-phosphates, heteropolyacids, sulfate metal oxides, mixed metal oxides, UZM-5, UZM-8, large pore molecular sieves, and mixtures thereof. An embodiment of the invention is one, any or all of prior embodiments in this paragraph up through the first embodiment in this paragraph, wherein the transalkylation catalyst comprises acidic clays selected from montmorillonite, beidellite, hectonite, saponite, and mixtures thereof. An embodiment of the invention is one, any or all of prior embodiments in this paragraph up through the first embodiment in this paragraph, wherein the transalkylation catalyst comprises a montmorillonite clay. An embodiment of the invention is one, any or all of prior embodiments in this paragraph up through the first embodiment in this paragraph, wherein the transalkylation temperature is from about 170° C. to about 200° C. An embodiment of the invention is one, any or all of prior embodiments in this paragraph up through the first embodiment in this paragraph, wherein the water source is introduced in an amount to provide from about 100 to about 120 wppm water. An embodiment of the invention is one, any or all of prior embodiments in this paragraph up through the first embodiment in this paragraph, wherein the feed stream comprises a benzene rich stream and a heavy alkylbenzene rich stream and the process further comprising a) contacting benzene and an olefin in an alkylation zone under alkylation conditions in the presence of an alkylation catalyst to produce an alkylation product comprising benzene, linear monoalkylbenzenes and heavy alkylbenzenes; b) passing the alkylation product to a benzene distillation column to provide a benzene column overhead stream and a benzene column bottoms stream; c) passing the benzene column bottoms stream to a paraffin distillation column to provide a paraffin column overhead stream and a paraffin column bottoms stream; and d) separating the paraffin column bottoms stream in an alkylbenzene distillation column to provide a monoalkylbenzene rich stream and the heavy alkylbenzene rich stream. An embodiment of the invention is one, any or all of prior embodiments in this paragraph up through the first embodiment in this paragraph, wherein the alkylation zone comprises at least a first alkylation reactor in an alkylation process cycle and at least a second alkylation reactor in a regeneration cycle. An embodiment of the invention is one, any or all of prior embodiments in this paragraph up through the first embodiment in this paragraph further comprising regenerating the at least second alkylation reactor by passing a benzene stream through the second alkylation reactor at a regeneration temperature above an alkylation temperature to provide a regeneration benzene stream, wherein the benzene rich stream comprises at least a portion of the regeneration benzene stream. An embodiment of the invention is one, any or all of prior embodiments in this paragraph up through the first embodiment in this paragraph further comprising passing the transalkylation reaction effluent to the benzene distillation column. An embodiment of the invention is one, any or all of prior embodiments in this paragraph up through the first embodiment in this paragraph, further comprising at least one of sensing at least one parameter of the process and generating a signal or data from the sensing; generating and transmitting a signal or generating and transmitting data.

A second embodiment of the invention is a process for transalkylating aromatic hydrocarbon compounds, the process comprising contacting benzene and an olefin in an alkylation zone under alkylation conditions in the presence of an alkylation catalyst to produce an alkylation product comprising benzene, linear monoalkylbenzenes and heavy alkylbenzenes; separating the alkylation product to provide a monoalkylbenzene rich stream and a heavy alkylbenzene rich stream; introducing a feed stream comprising a benzene rich stream from the alkylation zone and the heavy alkylbenzene rich stream to a transalkylation zone; introducing a water source to the transalkylation zone, the water source being in an amount to provide about 80 to about 120 wppm of water based upon the mass of the feed stream; and contacting the feed stream with a catalyst in the transalkylation zone under transalkylation conditions comprising a transalkylation temperature of from about 130° C. to about 230° C. including the presence of water to provide a transalkylation reaction effluent. An embodiment of the invention is one, any or all of prior embodiments in this paragraph up through the second embodiment in this paragraph, wherein the feed stream comprises benzene to heavy alkylbenzene in a molar ratio of about 15:1 to about 65:1. An embodiment of the invention is one, any or all of prior embodiments in this paragraph up through the second embodiment in this paragraph, wherein the transalkylation catalyst comprises a montmorillonite clay. An embodiment of the invention is one, any or all of prior embodiments in this paragraph up through the second embodiment in this paragraph, wherein the transalkylation temperature is from about 170° C. to about 200° C. An embodiment of the invention is one, any or all of prior embodiments in this paragraph up through the second embodiment in this paragraph, wherein the water source is introduced in an amount to provide from about 100 to about 120 wppm water. An embodiment of the invention is one, any or all of prior embodiments in this paragraph up through the second embodiment in this paragraph further comprising a) passing the alkylation product to a benzene distillation column to provide a benzene column overhead stream and a benzene column bottoms stream; b) passing the benzene column bottoms stream to a paraffin distillation column to provide a paraffin column overhead stream and a paraffin column bottoms stream; c) separating the paraffin bottoms column stream in an alkylbenzene distillation column to provide a monoalkylbenzene rich stream and the heavy alkylbenzene rich stream. An embodiment of the invention is one, any or all of prior embodiments in this paragraph up through the second embodiment in this paragraph, wherein the alkylation zone comprises at least a first alkylation reactor in an alkylation process cycle and at least a second alkylation reactor in a regeneration cycle. An embodiment of the invention is one, any or all of prior embodiments in this paragraph up through the second embodiment in this paragraph further comprising regenerating the second alkylation reactor by passing an benzene stream through the second alkylation zone at a regeneration temperature above an alkylation temperature to provide a regeneration benzene stream, wherein the benzene rich stream comprises at least a portion of the regeneration benzene stream. An embodiment of the invention is one, any or all of prior embodiments in this paragraph up through the first embodiment in this paragraph, further comprising at least one of sensing at least one parameter of the process and generating a signal or data from the sensing; generating and transmitting a signal or generating and transmitting data.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for transalkylating aromatic hydrocarbon compounds, the process comprising:
   introducing a heavy alkylbenzene rich stream and a benzene rich stream to a transalkylation zone;
   introducing a water source to the transalkylation zone, the water source being in an amount to provide 80 to 120 wppm of water based upon the mass of the feed stream;
   contacting the heavy alkylbenzene stream and the benzene stream with a transalkylation catalyst in the transalkylation zone under transalkylation conditions comprising a transalkylation temperature of greater than 130° C. to less than 230° C. in the presence of the water to provide a transalkylation reaction effluent; and
   wherein the deactivation rate of the transalkylation catalyst is less than 0.2 wt. %/hr and the conversion of heavy alkylbenzene is greater than 50 wt. %.

2. The process of claim 1, wherein the feed stream comprises benzene to heavy alkylbenzene in a molar ratio of about 15:1 to about 65:1.

3. The process of claim 1, wherein the transalkylation catalyst is selected from amorphous silica-alumina, fluorided amorphous silica-alumina, acidic clays, pillared clays, mesoporous crystalline materials, solid phosphoric acid, $AlCl_3$, alumino-phosphates, heteropolyacids, sulfate metal oxides, mixed metal oxides, UZM-5, UZM-8, large pore molecular sieves, and mixtures thereof.

4. The process of claim 1, wherein the transalkylation catalyst comprises acidic clays selected from montmorillonite, beidellite, hectonite, saponite, and mixtures thereof.

5. The process of claim 1, wherein the transalkylation catalyst comprises a montmorillonite clay.

6. The process of claim 1, wherein the transalkylation temperature is from about 170° C. to about 200° C.

7. The process of claim 1, wherein the water source is introduced in an amount to provide from about 100 to about 120 wppm water.

8. The process of claim 1, wherein the feed stream comprises a benzene rich stream and a heavy alkylbenzene rich stream and the process further comprising:
   contacting benzene and an olefin in an alkylation zone under alkylation conditions in the presence of an alkylation catalyst to produce an alkylation product comprising benzene, linear monoalkylbenzenes and heavy alkylbenzenes;
   passing the alkylation product to a benzene distillation column to provide a benzene column overhead stream and a benzene column bottoms stream;
   passing the benzene column bottoms stream to a paraffin distillation column to provide a paraffin column overhead stream and a paraffin column bottoms stream; and
   separating the paraffin column bottoms stream in an alkylbenzene distillation column to provide a monoalkylbenzene rich stream and the heavy alkylbenzene rich stream.

9. The process of claim 8, wherein the alkylation zone comprises at least a first alkylation reactor in an alkylation process cycle and at least a second alkylation reactor in a regeneration cycle.

10. The process of claim 9 further comprising regenerating the at least second alkylation reactor by passing a benzene stream through the second alkylation reactor at a regeneration temperature above an alkylation temperature to provide a regeneration benzene stream, wherein the benzene rich stream comprises at least a portion of the regeneration benzene stream.

11. The process of claim 8 further comprising passing the transalkylation reaction effluent to the benzene distillation column.

12. A process for transalkylating aromatic hydrocarbon compounds, the process comprising:
   contacting benzene and an olefin in an alkylation zone under alkylation conditions in the presence of an alkylation catalyst to produce an alkylation product comprising benzene, linear monoalkylbenzenes and heavy alkylbenzenes;
   separating the alkylation product to provide a monoalkylbenzene rich stream and a heavy alkylbenzene rich stream;
   introducing a feed stream comprising a benzene rich stream from the alkylation zone and the heavy alkylbenzene rich stream to a transalkylation zone;
   introducing a water source to the transalkylation zone, the water source being in an amount to provide 80 to 120 wppm of water based upon the mass of the feed stream;
   contacting the feed stream with a catalyst in the transalkylation zone under transalkylation conditions comprising a transalkylation temperature of from greater than 130° C. to less than 230° C. including the presence of water to provide a transalkylation reaction effluent; and wherein the deactivation rate of the transalkylation catalyst is less than 0.2 wt. %/hr and the conversion of heavy alkylbenzene is greater than 50 wt. %.

13. The process of claim 12, wherein the feed stream comprises benzene to heavy alkylbenzene in a molar ratio of about 15:1 to about 65:1.

14. The process of claim 12, wherein the transalkylation catalyst comprises a montmorillonite clay.

15. The process of claim 12, wherein the transalkylation temperature is from about 170° C. to about 200° C.

16. The process of claim 12, wherein the water source is introduced in an amount to provide from about 100 to about 120 wppm water.

17. The process of claim 12, wherein the step of separating comprises:
    passing the alkylation product to a benzene distillation column to provide a benzene column overhead stream and a benzene column bottoms stream;
    passing the benzene column bottoms stream to a paraffin distillation column to provide a paraffin column overhead stream and a paraffin column bottoms stream;
    separating the paraffin bottoms column stream in an alkylbenzene distillation column to provide the monoalkylbenzene rich stream and the heavy alkylbenzene rich stream.

18. The process of claim 12, wherein the alkylation zone comprises at least a first alkylation reactor in an alkylation process cycle and at least a second alkylation reactor in a regeneration cycle.

19. The process of claim 18 further comprising regenerating the second alkylation reactor by passing a benzene stream through the second alkylation zone at a regeneration temperature above an alkylation temperature to provide a regeneration benzene stream, wherein the benzene rich stream comprises at least a portion of the regeneration benzene stream.

20. The process of claim 1, further comprising at least one of:
    sensing at least one parameter of the process and generating a signal or data from the sensing;
    generating and transmitting a signal; or
    generating and transmitting data.

* * * * *